United States Patent [19]
> Edgren et al.

[11] Patent Number: 4,946,685
[45] Date of Patent: * Aug. 7, 1990

[54] CELLULOSIC DOSAGE FORM

[75] Inventors: David E. Edgren, El Granada; Judy A. Magruder, Mt. View; Gurdish K. Bhatti, Fremont, all of Calif.

[73] Assignee: Alza Corporation, Palo Alto, Calif.

[*] Notice: The portion of the term of this patent subsequent to Nov. 22, 2005 has been disclaimed.

[21] Appl. No.: 239,231

[22] Filed: Sep. 1, 1988

Related U.S. Application Data

[63] Continuation-in-part of Ser. No. 34,971, Apr. 6, 1987, Pat. No. 4,786,503.

[51] Int. Cl.⁵ ............................................. A61K 9/24
[52] U.S. Cl. ..................................... 424/472; 424/473
[58] Field of Search ................................ 424/472, 473

[56] References Cited

U.S. PATENT DOCUMENTS

| | | | |
|---|---|---|---|
| 3,870,790 | 3/1975 | Lowey et al. | 424/19 |
| 4,140,755 | 2/1979 | Sheth et al. | 424/21 |
| 4,167,558 | 9/1979 | Sheth et al. | 424/22 |
| 4,226,849 | 10/1980 | Schor | 424/19 |
| 4,259,314 | 3/1981 | Lowey | 424/19 |
| 4,357,469 | 11/1982 | Schor | 536/91 |
| 4,369,172 | 1/1983 | Schor et al. | 424/19 |
| 4,389,393 | 6/1983 | Schor et al. | 424/19 |
| 4,454,108 | 6/1984 | Iida et al. | 424/16 |
| 4,540,566 | 9/1985 | Davis et al. | 424/22 |
| 4,610,870 | 9/1986 | Jain et al. | 424/19 |
| 4,693,895 | 9/1987 | Wong et al. | 424/473 |
| 4,786,503 | 11/1988 | Edgren et al. | 424/472 X |

FOREIGN PATENT DOCUMENTS 0074584 3/1982 European Pat. Off. ............ 424/472

*Primary Examiner*—Thurman K. Page
*Attorney, Agent, or Firm*—Edward L. Mandell; Steven F. Stone; Paul L. Sabatine

[57] ABSTRACT

A bilaminate dosage form is disclosed comprising a first lamina and a second lamina with each lamina comprising a cellulose ether composition, and wherein a drug is present in at least one of the lamina. An optional coat is disclosed that surrounds the bilaminate form.

14 Claims, 5 Drawing Sheets

4,946,685

CELLULOSIC DOSAGE FORM

CROSS-REFERENCE TO RELATED APPLICATIONS

This application is a continuation-in-part of U.S. patent application Ser. No. 07/034,971 filed on Apr. 6, 1987, now U.S. Pat. No. 4,786,503 issued Nov. 22, 1988 which application is incorporated herein by reference and benefit is claimed of its filing date. This application is copending with U.S. patent application Ser. No. 07/039,405 filed on Apr. 17, 1987 now U.S. Pat. No. 4,871,548 issued Oct. 3, 1989. These applications are assigned to the ALZA Corporation of Palo Alto, California.

FIELD OF THE INVENTION

This invention pertains to a controlled release dosage form. More particularly, the invention concerns a dosage form comprising a first composition manufactured as a first lamina and a second composition manufactured as a second lamina, in laminated arrangement. The first composition or lamina comprises a cellulose ether composition and the second composition or lamina comprises a presently preferred different cellulose ether composition. The invention relates also to a dosage form comprising a coating that surrounds the first lamina and the second lamina. A dosage amount of drug is present in at least one of the lamina.

BACKGROUND OF THE INVENTION

Dosage forms, often manufactured in the shape of a compressed single layered tablet, comprising a cellulose ether are known to the pharmaceutical drug dispensing art. For example, dosage forms comprising the cellulose ether hydroxypropylmethylcellulose are disclosed in U.S. Pat. Nos. 3,870,790; 4,140,755; 4,167,588; 4,226,849; 4,259,314; 4,357,469; 4,369,172; 4,389,393 and U.S. Pat. No. 4,540,566.

While the dosage forms known to the prior art use the cellulose ether hydroxypropylmethylcellulose there are major disadvantages associated with the prior art dosage forms. For instance, the mechanical integrity of some prior art dosage forms often is insufficient to provide both a sustained and a controlled release of drug over a prolonged period of time. The prior art dosage forms often exhibit insufficient mechanical integrity, that is, the ability to stay together in a moving fluid environment such as the gastrointestinal tract, without prematurely breaking-up and thereby prematurely releasing all of its drug. The above-mentioned desirable properties of sustained and controlled release are not apparent in the prior art dosage forms that undergo substantial disintegration, often in less than eight hours, in a fluid environment of use.

Another disadvantage associated with the prior art dosage forms is that the dosage forms frequently exhibit an unwanted, variable and difficult to reproduce drug release rate pattern. For example, the prior art dosage forms comprising a small amount of a cellulose ether frequently exhibit the above behavior, such as those dosage forms containing less than five weight percent (wt %) hydroxypropylmethylcellulose having a molecular weight greater than 50,000 grams per mole and blended with a hydroxypropylmethylcellulose having a molecular weight much less than 50,000. The presence of the high molecular weight polymer in the dosage form masks the release characteristics of the low molecular weight polymer in the dosage form resulting in an erratic release rate pattern which is difficult to reproduce from dosage form to dosage form and from batch to batch comprising the dosage forms.

Still other disadvantages associated with the prior art dosage forms are that the dosage form over its shelf-life can exhibit an unpredictable change in its release rate characteristics; the prior art dosage forms, when tested in an in vitro test that substantially reproduces the in vivo environment of the gastrointestinal tract, often release the drug at a greater rate of release in vivo rather than in vitro, which difference can be attributed to a premature disintegration of the prior art dosage form; and, the prior art dosage form in a high shear fluid environment, such as the stomach, releases its drug too quickly, usually in less than four hours and it is, therefore, not adapted to prolonged drug release.

Thus, in the light of the above presentation, it will be appreciated by those versed in the dispensing art that if a novel dosage form is made available to the medical and pharmaceutical arts for dispensing difficult to deliver drugs essentially-free of the tribulation known to the prior art, such a dosage form would have a definite use and also would be a valuable contribution to the dispensing art. It will be further appreciated by those versed in the dispensing art that if a dosage form can be provided that (a) possesses desirable release rate and mechanical properties for dispensing a drug over a prolonged period of time, (b) provide instant drug availability and prolonged drug delivery from the same dosage form, and which dosage form (c) can be manufactured at an economical cost, such a dosage form would have a positive and a practical value and represent an advancement in the pharmaceutical arts.

OBJECTS OF THE INVENTION

Accordingly, it is an immediate object of this invention to provide a novel dosage form for the controlled delivery of a beneficial drug to a biological environment of use, and which dosage form represents an improvement and an advancement in the delivery arts.

Another object of the invention is to provide both a novel and a useful dosage form that overcomes the difficulties associated with the prior art.

Another object of the invention is to provide a dosage form comprising a first lamina and a second lamina, which laminae comprise a cellulose ether composition with at least one of the laminae comprising a dosage unit amount of a beneficial drug.

Another object of this invention is to provide a dosage form that is useful for delivering a beneficial drug formulation that is difficult to deliver and now can be delivered by the dosage form of this invention at a meaningful therapeutic rate over a prolonged period of time.

Another object of the present invention is to provide a dosage form comprising a beneficial drug that can be from insoluble to very soluble in an aqueous fluid, and which drug can be delivered by the dosage form at an in vivo rate of release that is substantially the equivalent of the in vitro rate of release.

Another object of this invention is to provide a dosage form that can administer to a warm-blooded host a complete pharmaceutical regimen, comprising very soluble or poorly soluble drugs, at a controlled and continuous rate for a particular time period, the use of which requires intervention only for initiation and possible termination of the regimen.

Another object of the present invention is to provide a dosage form for delivering a drug in the gastrointestinal tract that substantially avoids a premature break-up and undergoes a controlled change in its integrity at a rate corresponding to the controlled rate of release of drug over a prolonged period of time of at least six hours.

Another object of the invention is to provide a dosage form that can administer a drug at an immediate period of time followed by administering drug at a rate-controlled dose over a prolonged period of time.

Another object of the invention is to provide a dosage form comprising means for immediate drug therapy and succeeding continuous prolonged drug therapy.

Another object of the invention is to provide a dosage form comprising an exterior coat that surrounds internal means, which exterior coat is a means for administering a drug in a short period of time followed by the external means administering a drug over a longer period of time.

Other objects, features, aspects and advantages of the invention will be more apparent to those versed in the dispensing art from the following detailed specification taken in conjunction with the drawing figures and the accompanying claims.

BRIEF DESCRIPTION OF THE DRAWINGS

In the drawings, which are not drawn to scale but are set forth to illustrate various embodiments of the invention, the drawing figures are as follows.

In the drawings and in the specification like parts in related figures are identified by like numbers. The terms appearing earlier in the specification and in the drawings, as well as embodiments thereof, are further described elsewhere in this specification.

DETAILED DESCRIPTION OF THE DRAWINGS

Figure 1:
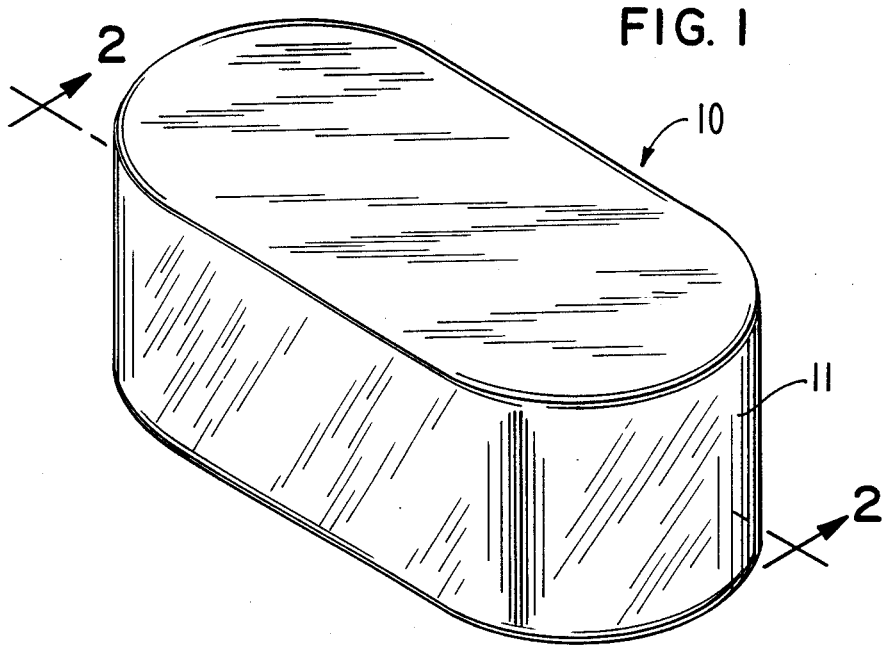
FIG. 1 is a side, elevated view of a dosage form provided by this invention, designed and shaped for orally administering a beneficial drug to the gastrointestinal tract of a recipient.

Turning now to the drawing figures in detail, which drawing figures are an example of the dosage forms provided by the invention and which example is not to be construed as limiting, one example of this dosage form is illustrated in FIG. 1, designated by the numeral 10. In FIG. 1, dosage form 10 comprises body 11. Dosage form 10 can be manufactured into various sizes and shapes adapted for oral admittance into the gastrointestinal tract of a warm-blooded animal. For example, dosage form 10 can be of any convenient geometric shape, such as ellipsoid, bean-shaped, circular-shaped, rectangular-shaped, caplet-shaped, and the like.

Figure 2:
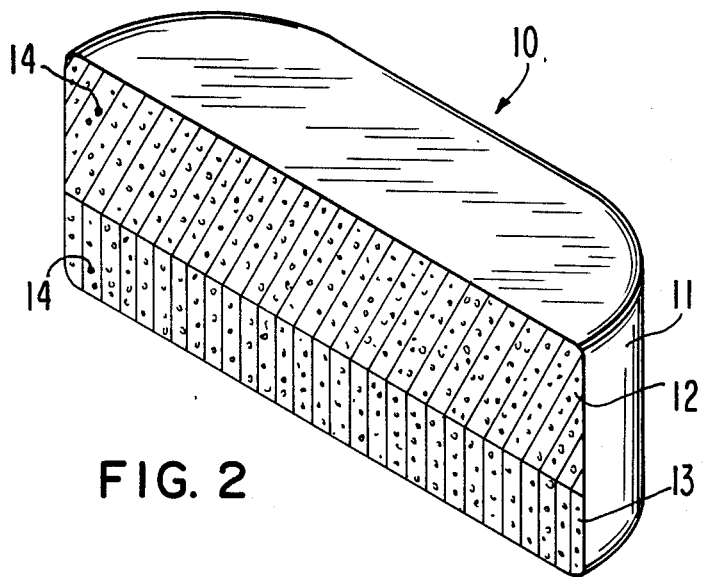
FIG. 2 is an opened view of the dosage form of FIG. 1 through 2—2 of the dosage form for illustrating the internal structure of the dosage form.

In FIG. 2, dosage form 10 of FIG. 1 is seen in opened section through 2—2 of FIG. 1. In FIG. 2 dosage form 10 comprises body 11, which body 11 comprises a first composition manufactured as a lamina 12 and a second composition made as a lamina 13. First lamina 12 and second lamina 13 are mated together and they function initially in concert as a single dosage form 10. Dosage form 10 comprises at least one beneficial drug 14 present in at least one of first lamina 12, or present in second lamina 13 or, optionally, present in both first lamina 12 and in second lamina 13. Dosage form 10 comprising lamina 12 and lamina 13 comprises at least one non-toxic cellulose ether composition and, optionally, other pharmaceutically acceptable laminae forming ingredients.

Dosage form 10 comprises from about 10 weight percent to 90 weight percent (wt %) of at least one cellulose ether composition based on the total weight of the dosage form. In a presently preferred embodiment the cellulose ether composition of dosage form 10 comprises at least one hydroxypropylmethylcellulose and, optionally, at least one hydroxypropylcellulose. The hydroxypropylmethylcellulose operable for the purpose of this invention comprises a hydroxypropoxyl content of 4% to 12% and a methoxyl content of 19% to 30%. The hydroxypropylcellulose comprises a hydroxypropxyl content of from 7% to 16%. Exemplary hydroxypropylmethylcellulose that can be used for forming lamina of dosage form 10 comprises at least one of a member selected from the group consisting of (a) a hydroxypropylmethylcellulose having a degree of polymerization (DP) of about 50, a viscosity of about 3 centipoises (cps) of a 2% solution in water, and a number average molecular weight of about 9,200; (b) a hydroxypropylmethylcellulose having a DP of 100, a viscosity of 35 centipoises, and a number average molecular weight ($MW_n$) of 19,600; (c) a hydroxypropylmethylcellulose comprising a DP of 145, a viscosity of 100 cps, and a $MW_n$ of 27,800; (d) a hydroxypropylmethylcellulose comprising a DP of 460, a viscosity of 4,000 cps, and a $MW_n$ of 88,300; (e) a hydroxypropylmethylcellulose comprising a DP of 690, a viscosity of 15,000 cps, and a $MW_n$ of 132,500; and (f) a hydroxypropylmethylcellulose having a DP of 1,260, a viscosity of 100,000 cps and a $MW_n$ of 242,000.

Other hydroxypropylmethylcellulose ethers that can be used for the purpose of providing dosage form 10 are (g) a hydroxypropylmethylcellulose comprising a DP of 59, a viscosity of 6 and a $MW_n$ of 11,900; and (h) a hydroxypropylmethylcellulose possessing a DP of 860, a viscosity of 30,000 and a $MW_n$ of 165,000. The examples set forth above generally comprise a hydroxypropylmethylcellulose comprising a DP of 40 to 1600, a viscosity of 2 to 225,000 and a $MW_n$ of from 7,680 to 307,200 and mixtures thereof.

The hydroxypropylcellulose used for the purpose of this invention is a non-ionic ether with neutral pH range and a hydroxypropyl content of 7% to 16%, with more specific hydroxypropylcelluloses examples comprising a hydroxypropyl content of 7% to 10%; a hydroxypropyl content of 10% to 13%, and a hydroxypropyl content of 13% to 16%. In the above specification DP is the degree of polymerization indicating the average number of monomers polymerized in the final polymer.

Lamina 12 of dosage form 10 comprises at least one hydroxypropylmethylcellulose in an amount of at least 15 wt % to 80 wt % based on the total weight of dosage form 10, or at least 20 wt % to 80 wt % based on the total weight of lamina 12. Lamina 13 of dosage form 10 comprises at least one hydroxypropylcellulose, or at least one hydroxypropylmethylcellulose, in an amount of at least 2 wt % to 60 wt % based on the total weight of dosage form 10, or about 5 wt % to 50 wt % based on the total weight of lamina 13. Lamina 12 and lamina 13 can comprise each a single cellulose ether, a blend of two cellulose ethers, a tertiary blend comprising three cellulose ethers, and the like. Lamina 12 and lamina 13 in a preferred embodiment comprise unlike cellulose ethers, can comprise like cellulose ether with the proviso that the final lamina are different in respect to ratios, amounts, thickness or the like.

Representative of cellulose ether compositions comprising lamina 12 are (a) a composition comprising a hydroxypropylmethylcellulose having a $MW_n$ of about 242,000; (b) a hydroxypropylmethylcellulose having a $MW_n$ of about 132,500; (c) a composition comprising both a hydroxypropylmethylcellulose having a $MW_n$ of 9,200 and a hydroxypropylmethylcellulose having a $MW_n$ of 242,000; (d) a composition comprising a hydroxypropylmethylcellulose having a $MW_n$ of 19,600 and a hydroxypropylmethylcellulose having a $MW_n$ of about 242,000; (e) a composition comprising a hydroxypropylmethylcellulose having a $MW_n$ of about 27,800 and a hydroxypropylmethylcellulose having a $MW_n$ of about 242,000; (f) a composition comprising a hydroxypropylmethylcellulose having a $MW_n$ of 88,300 and a hydroxypropylmethylcellulose having a $MW_n$ of about 242,000; (g) a composition comprising a hydroxypropylmethylcellulose having a $MW_n$ of 132,500 and a hydroxypropylmethylcellulose having a $MW_n$ of about 242,000; (h) a composition comprising a hydroxypropylmethylcellulose having a $MW_n$ 9,200 and a hydroxypropylmethylcellulose having a $MW_n$ of 19,600 and a hydroxypropylmethylcellulose having a $MW_n$ of about 242,000; (i) a composition comprising a hydroxypropylmethylcellulose having a $MW_n$ of 9,200, a hydroxypropylmethylcellulose having a $MW_n$ of 88,300 and a hydroxypropylmethylcellulose having a $MW_n$ of about 242,000; (j) a composition comprising a hydroxypropylmethylcellulose having a $MW_n$ of 19,600, a hydroxypropylmethylcellulose having a $MW_n$ of about 27,800 and a hydroxypropylmethylcellulose having a $MW_n$ of about 242,000; and the like. In a presently preferred embodiment lamina 12 comprises a binary composition comprising two cellulose ethers comprises from 1 wt % to 99 wt % of one cellulose ether and from 99 wt % to 1 wt % of the other cellulose ethers. In another presently preferred embodiment lamina 12 comprises a tertiary composition comprising from 1 wt % to 99 wt % of each cellulose ether with a total cellulose ether content of up to 80 wt % based on the total weight of lamina 12.

Lamina 13, in one presently preferred embodiment, comprises from 2 wt % to 60 wt % of a cellulose ether such as a low substituted hydroxypropylcellulose ether having a hydroxypropyl content of 7% to 16% neat or in composition with a different cellulose ether or a hydroxypropylmethylcellulose. Lamina 13 can, optionally, comprise at least one hydroxypropylmethylcellulose. Lamina 13 in other preferred embodiments comprises (a) a binary blend of hydroxypropylcellulose having a hyroxypropyl content of 7 wt % to 10 wt % blended with a hydroxypropylcellulose having a hydroxypropyl content of 13 wt % to 16 wt %; (b) a composition comprising a hydroxypropylcellulose having a hydroxypropyl content of 7 wt % to 10 wt % blended with a hydroxypropylcellulose having a hydroxypropyl content of about 10 wt % to 13 wt %; (c) a composition comprising a hydroxypropylcellulose and a hydroxypropylmethylcellulose having a $MW_n$ of 9,200; (d) a composition comprising a hydroxypropylcellulose and a hydroxypropylmethylcellulose having a $MW_n$ of about 19,600; (e) a composition comprising a hydroxypropylcellulose and a hydroxypropylmethylcellulose having a $MW_n$ of 27,800; (f) a composition comprising a hydroxypropylcellulose and a hydroxypropylmethylcellulose having a $MW_n$ of about 88,300; (g) a composition comprising a hydroxypropylcellulose and a hydroxypropylmethylcellulose having a $MW_n$ of about 132,500; (h) a composition comprising a hydroxypropylcellulose and a hydroxypropylmethylcellulose having a $MW_n$ of about 242,000; (i) a composition comprising a hydroxypropylmethylcellulose blended with a different hydroxypropylmethylcellulose with the proviso that lamina 13 is different from lamina 12.

Dosage form 10 in another embodiment is designed for delivering at least one drug to a biological receptor, and in this embodiment dosage form 10 comprises in first lamina 12 at least one hydroxypropylmethylcellulose comprising a degree of polymerization of 40 to 1600, a viscosity of 2 to 225,000, and a molecular weight of 7,680 to 307,200; and second lamina 13 comprises at least one hydroxypropylmethylcellulose comprising a degree of polymerization of 40 to 1600, a viscosity of 2 to 225,000 and a molecular weight of 7,680 to 307,200. In this embodiment, dosage form 10 is provided with the presently optional preferred proviso that (a) lamina 12 or lamina 13 comprises at least one different hydroxypropylmethylcellulose, or that (b) lamina 12 and/or lamina 13 comprise hydroxypropylmethylcellulose in different lamina forming drug releasing ratios.

Figure 3:
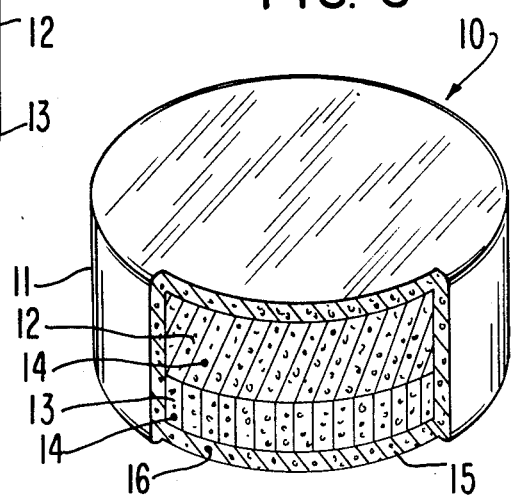
FIG. 3 is an opened view of a dosage form provided by the invention which dosage form comprises a bilayer surrounded by a coat.

FIG. 3 illustrates another manufacture provided by the invention. In FIG. 3, a dosage form 10 is seen in opened view and it comprises body 11, first lamina 12, a drug 14 in first lamina 12, second lamina 13 and a drug 14 in second lamina 13. Drug 14 present in first lamina 12 and in second lamina 13 may be the same or different. In FIG. 3, dosage form 10 additionally comprises an external coat 15. Coat 15 surrounds internal lamina 12 and internal lamina 13. External coat 15 enhances the properties of dosage form 10 by substantially preventing edge clipping of lamina 12 or lamina 13; coat 15 promotes lamination integrity; it functions to prevent premature drug release; coat 15 increases shelf-life by substantially preventing air and water from entering dosage form 10 during storage; it masks the unpleasant taste of drugs; it helps lessen tackiness, and it provides cosmetic elegance. Coat 15 comprises at least one hydroxypropyl(alkyl)$_n$-cellulose, wherein n is 0 or 1 and alkyl is straight or branched of 1 to 7 carbons, such as methyl, ethyl, etc., and at least one pharmaceutically acceptable plasticizer for imparting flexibility to dosage form 10, to facilitate processing and to increase toughness of coat 15. Representative plasticizers include acetylated monoglycerides, monoglycerides, glycerol monostearate, acetylated triglycerides, polyethylene glycol, triethyl citrate, glycerol, triacetin, lecithin, propylene glycol, and the like. The presently preferred plasticizers are dispersible in a water solution comprising the hydroxypropyl(alkyl)$_n$ cellulose. Generally, from 2% to 40% of plasticizer is mixed with the hydroxypropyl(al )$_n$ cellulose. Other agents can optionally be included to enhance mechanical, cosmetic, or taste-mask quality of the silicone coat such as polishing agents, filmformers, opacifiers, wetting agents and flavors. Polishing agents include carnauba wax and beeswax. Examples of additional film-formers include shellac, polyvinylpyrrolidone, and sodium carboxymethylcellulose. Examples of opacifying agents include titanium dioxide, silicone dioxide, iron oxide, and aluminum lake dyes. Surfactants include sodium lauryl sulfate, polysorbates, and the like. Flavor enhancing components include sucrose, sorbitol, mannitol, and natural and synthetic essential flavors such as peppermint or lime. The coating fluid can be spray coated, dip coated, and the like, around the bilaminate to provide coated 15 dosage form 10. In FIG. 3, dosage form 10 comprises optional drug 16 in coat 15. The presence of drug 16 provides instant drug release when dosage form 10 is introduced into an aqueous environment of use. The instant drug 16 is supplemental to the instant and prolonged drug delivery of dosage form 10, for improved drug therapy. Dosage form 10 comprises at least one beneficial drug 14. Drug 14 can be presented in lamina 12 or drug 14 can be presented in lamina 13, or drug 14 can be presented in both lamina 12 and lamina 13. In this specification the term, "drug," includes any physiological or pharmacologically active substance that produces a local or systemic effect in animals, including warm-blooded mammals, humans and primates; avians; household, sport and farm animals; laboratory animals; fishes; reptiles; and zoo animals. The term, "physiologically," as used herein, denotes the administration of a drug to produce generally normal levels and functions in a warmblooded animal. The term, "pharmacologically," generally denotes variations in response to the amount of drug administered to the host. See *Stedman's Medical Dictionary*. (1966), published by Williams and Wilkins, Baltimore, MD.

The beneficial drug that can be delivered from dosage form 10 includes inorganic and organic compounds without limitation, including drugs that act on peripheral nerve, adrenergic receptors, cholinergic receptors, the nervous system, skeletal muscles, the cardiovascular system, smooth muscles, the blood circulatory system, synaptic sites, neuroeffector junctional sites, the endocrine system, hormone systems, the immunological system, organ systems, the reproductive system, the skeletal system, autocoid systems, the alimentary system, excretory system, and as inhibitors of autocoids and histamine systems. The active drug that can be delivered for acting on these recipients include anticonvulsants, analgesics, anti-Parkinsons, antiinflammatories, anesthetics, antimicrobials, antimalarials, antiparasitic, antihypertensives, angiotensin converting enzyme inhibitor, antihistamines, antipyretics, alpha-adrenergic agnoist, alpha-blockers, biocides, bactericides, bronchial dilators, betaadrenergic stimulators, beta-adrenergic blocking drugs, contraceptives, cardiovascular drugs, calcium channel inhibitors, depressants, diagnostics, diuretics, electrolytes, hypnotics, hormonals, hyperglycemics, muscle contractants, muscle relaxants, opthalmics, psychic energizers, parasympathomimetics, sedatives, sympathomimetics, tranquilizers, urinary tract drugs, vaginal drugs, vitamins and the like.

Exemplary drugs that are very soluble in water and can be delivered by dosage form 10 of this invention include prochlorperazine edisylate, ferrous sulfate, aminocaproic acid, potassium chloride, mecamylamine, hydrochloride, procainamide hydrochloride, amphetamine sulfate, benzphetamine hydrochloride, isoproteronol sulfate, methamphetamine hydrochloride, phenmetrazine hydrochloride, atropine sulfate, scopolamine bromide, isopropamide iodine, tridihexethyl chloride, phenformin hydrochloride, methylphenidate hydrochloride, cimetidine hydrochloride, codeine phosphate, theophylline cholinate, phenylpropanolamine and its acid addition salts, cephalexin hydrochloride, phenylpropanolamine hydrocloride, chlorpheniramine, chlorpheniramine and its therapeutically acceptable salts, chlorpheniramine maleate, and the like.

Exemplary drugs that are poorly soluble in water and that can be delivered by dosage form 10 of this invention include diphenidol, meclizine hydrochloride, prochlorperazine maleate, phenoxybenzamine, thiethylperazine maleate, anisindone, diphenadione, erythrityl tetranitrate, digoxin, isoflurophate, acetazolamide, methazolamide, bendroflumethiazide, chlorpropamide, tolazamide, chlormadinone acetate, penaglycodol, allopurinol, aluminum aspirin, methotrexate, acetyl sulfisoxazole, erythromycin, progestins, esterogenic, progestational, corticosteroids, hydrocortisone, hydrocorticosterone acetate, cortisone acetate, triamcinolone, methyltesterone, 17-beta-estradiol, ethinyl estradiol, prazosin hydrochloride, ethinyl estradiol 3-methyl ether, pednisolone, 17-alpha-hydroxyprogesterone acetate, 19-nor-progesterone, norgestrel, norethindrone, progesterone, norgesterone, levonorgestrel, norethynodrel, and the like.

Examples of other preferred drugs that can be delivered by dosage form 10 include nonsteroidal antiinflammatories, aspirin, indomethacin, naproxen, fenoprofen, sulindac, indoprofen, nitroglycerin, propranolol, timolol, atenolol, alprenolol, cimetidine, clonidine, imipramine, levodopa, chloropromazine, methyldopa, dihydroxyphenylalnine, pivaloyloxyethyl ester of alpha-methyldopa, theophylline, calcium gluconate, ketoprofen, ibuprofen, cephalexin, erythromycin, haloperidol, zomepirac, ferrous lactate, vincamine, diazepam, captopril, phenoxybenzamine, nifedipine, diltiazem, acetaminophen, verapamil, milrinone, madol, quanbenz, hydrochlorothiazide, and the like. The beneficial drugs are known to the art in *Pharmaceutical Sciences*, 14th Ed., edited by Remington, (1979), published by Mack Publishing Co., Easton, PA; *The Drug, The Nurse, The Patient, Including Current Drug Handbook*, by Falconer et al., (1974–1976) published by Sunder Co., Philadelphia, PA; *Medicinal Chemistry*, 3rd Ed., Vols. 1 and 2, by Burger, published by WileyInterscience, New York; and in *Physicians'Desk Reference*, 38th Ed., (1984), published by Medical Economics Co., Oradell, NJ.

The drug 14 in dosage form 10 can be in various nontoxic forms, such as uncharged molecules, molecular complexes, pharmacologically acceptable salts such as hydrochloride, hydrobromide sulfate, laurate, palmitate, phosphate, nitrite, borate, acetate, maleate, tartrate, oleate and salicylate. For acidic drugs, salts of metals, amines or organic cations; for example, quaternary ammonium can be used. Derivatives of drugs such as ester, ethers and amides can be used in dosage form 10. Also, a drug that is water insoluble can be used in a form that is a water soluble derivative thereof to serve as a solute, and on its release from dosage form 10 is converted by enzymes, hydrolyzed by body pH or other metabolic processes to the original therapeutically active form.

Drug 14 can be present in dosage form 10 neat or, in a presently preferred optional embodiment, with other composition and lamina forming ingredients, such as a binder, a filler, a dispersant, a surfactant, a wetting agent, a lubricant or a dye. Representative of these include acacia, agar, calcium carrageenan, alginic acid, algin, agarose powder, microcrystalline cellulose, collagen, colloidal magnesium silicate, colloidal silicon dioxide, pectin, gelatin, calcium sulfate, lactose, mannitol, ethyl cellulose, ethyl cellulose having a 45 to 49.5 weight percent ethoxy content, and the like; binders like polyvinyl pyrrolidone or starch; lubricants such as magnesium stearate; wetting agents such as fatty amines, fatty quaternary ammonium salts, esters of sorbitol, and the like. The phrase, "drug formulation," includes the drug is present in dosage form 10 neat, or accompanied by a binder, and the like. The amount of beneficial drug in dosage form 10 generally is from about 0.05 ng to 5 g or more, with individual dosage form 10 comprising, for example, 25 ng, 1 mg, 5 mg, 10 mg, 25 mg, 250 mg, 750 mg, 1.0 g, 1.2 g, 1.5 g, and the like. In one presently preferred embodiment lamina 12 comprises more drug 14 than lamina 13; however, the amount of drug 14 can be the same in lamina 12 and in lamina 13. Generally, in one presently preferred embodiment, the amount of drug will be in a ratio in lamina 12 to lamina 13 of 1.1 to 15.1. The dosage form can be administered once, twice, three times daily, and the like.

Dosage form 10 is manufactured by first making independently lamina 12, or lamina 13, which laminae are made from a composition of laminae forming members. For example, a particular lamina is made as follows: first, each of the ingredients comprising a lamina are independently screened and then blended together, except for the lubricant. Then, the blend is wet granulated by adding a solvent such as anhydrous ethanol, and the wet ingredients mixed until a blend is obtained by said process. Next, the wet blend is passed through a screen and dried to evaporate the solvent. The resulting granules are passed again through a sieve. Next, a small amount of a finely divided lubricant is added to the dry granules and the lubricant and granules blended to provide a drug composition. The above described procedure is repeated for the other lamina.

Next, the two lamina forming compositions are fed independently into separate hoppers of a compression machine. The machine lightly compresses one lamina and then adds the second lamina forming granulation in laminating arrangement to the first lamina and then compresses the two laminae together. Typically, about one to three tons of pressure are applied to laminate the laminae and yield the final dosage form.

The dosage form can be made also by a dry granulation process of manufacture. The dry process comprises first mixing, for a particular lamina, all the lamina forming ingredients, except for the lubricant; passing the mixed ingredients through a grinding mill to a small mesh size and then transferring the sized powder to a dry compactor. The compactor densifies the powder, which dense powder then is passed through a sizing mill to regrind the composition. The composition is ground to a small size, typically 20 mesh or smaller. Finally, a dry lubricant is added and the ingredients blended to produce the final lamina forming composition. The second lamina is made in a similar manner. Then, each composition is fed independently to the compaction press and compressed into the dosage form comprising parallel laminae. A lamina comprising at least one cellulose ether or more than one cellulose ether is manufactured in the mode and manner of the above-described procedures.

Other standard manufacturing procedures can be used to form the laminae and the laminated dosage form. For example, the various ingredients can be mixed with a solvent by fluidized bed, granulating, ballmilling, calendering, stirring or rollmilling, and then pressed into a preselected size and shaped lamina. A second lamina made in a like process comprising a shape and size corresponding to the first lamina is then laminated with pressure to the first lamina to yield the dosage form.

Exemplary solvents suitable for manufacturing the lamina, on the coat, include inorganic and organic solvents that do not adversely harm the lamina, the lamina forming ingredients and the final dosage form. The solvents broadly include a member selected from the group consisting of alcohols, ketones, esters, ethers, aliphatic hydrocarbons, halogenated solvents, cycloaliphatic solvents, aromatics, heterocyclic solvents, water, and mixtures thereof. Typical solvents include acetone, diacetone, methanol, ethanol, isopropyl alcohol, butyl alcohol, methyl acetate, ethyl acetate, isopropyl acetate, n-butylacetate, methyl isobutyl ketone, methyl propyl ketone, n-hexane, n-heptane, methylene dichloride, ethylene dichloride, propylene dichloride, ethyl ether, mixtures such as acetone and ethanol, water and ethanol, acetone and methanol, methylene dichloride and methanol, ethylene dichloride and methanol, and the like.

The following examples illustrate means and methods for carrying out the present invention. The examples are merely illustrative and they should not be considered as limiting the scope of the invention, as these examples and other equivalents thereof will become more apparent to those versed in the pharmaceutical dispensing art in the light of the present disclosure, the drawings and the accompanying claims.

EXAMPLE 1

A lamina forming composition comprising 29.5 wt % isosorbide dinitrate; 29.5 wt % lactose; 40.0 wt % hydroxypropylmethylcellulose, having an average molecular weight of 27,800; and 1.0 wt % magnesium stearate is compressed into a first lamina. Next, a different and second lamina forming composition comprising 97.0 wt % hydroxypropylmethylcellulose, having a molecular weight of 242,000; 1.0 wt % ferric oxide and 2.0 wt % magnesium stearate is deposited over the first described lamina, and the second lamina laminated to the first lamina with a compression of 2 tons. The first lamina weighed 271 mg and the second lamina weighed 100 mg. The laminae are compressed in a 13/32 inch round dye. The dosage form release pattern measured in a shaking flask containing water and a few marbles to produce mechanical abuse, exhibited a cumulative release of 98% over a 24 hour period of time. Lamina 1, comprising the lower molecular weight cellulose ether 27,800, erodes in the aqueous environment and administers the drug over a short time. Lamina 2, comprising the higher molecular weight ether having a molecular weight of 241,000, maintains its mechanical integrity longer because of its composition. Lamina 2 comprising the higher molecular weight cellulose also serves as a support member for lamina 1 comprising the lower molecular weight cellulose ether.

EXAMPLE 2

Figure 4:
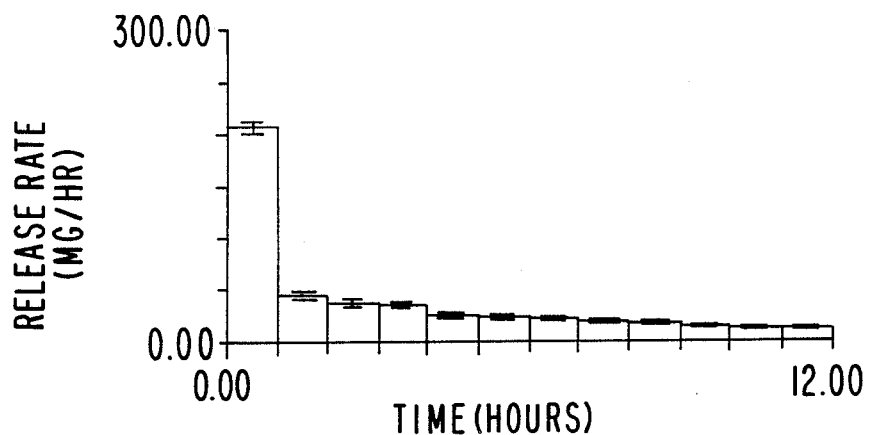
FIG. 4 is a graph that depicts the release rate pattern comprising an immediate dose of drug followed by controlled and continuous delivery of drug over a prolonged period of time.
Figure 5:
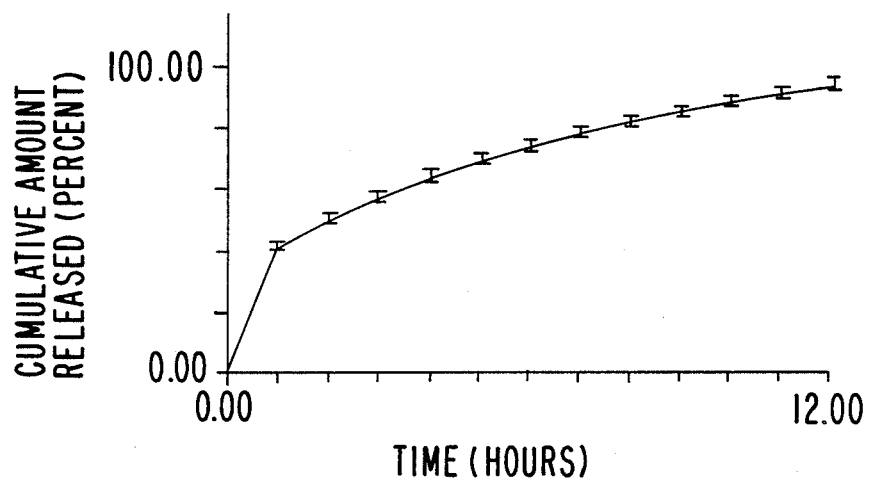
FIG. 5 is a graph that illustrates the cumulative amount of drug released by a dosage form over a prolonged period of at least twelve hours.

The procedures described above are followed in this example. First, a lamina forming composition comprising 58.0 wt % acetaminophen; 25.0 wt % hydroxypropylmethylcellulose, having a number average molecular weight of 242,000, a number average degree of polymerization of about 1260 and a viscosity of 100,000 centipoises; 15.0 wt % hydroxypropylmethylcellulose, having a number average molecular weight of 9,200, a number average degree of polymerization of 50 and a viscosity of 3 centipoises; and, 2.0 wt % magnesium stearate is compressed into a first lamina. The lamina weighed 604 mg. Then, a second lamina forming composition weighing 170.5 mg and comprising 88.0 wt % acetaminophen; 10.0 wt % hydroxypropylcellulose with a 10–13 wt % hydroxypropxy content, and 2.0 wt % magnesium stearate is laminated to the first lamina to yield the dosage form. The release rate pattern measured in mg/hr for this bilaminated dosage form over a 12 hour period of time is depicted in FIG. 4. The cumulative amount of acetaminophen released on a percent basis is depicted in FIG. 5. The dosage form exhibited an initial release of 200 mg drug within the first hour, followed by a mean release rate of 24 mg per hour for the next eleven hours.

EXAMPLE 3

Figure 6:
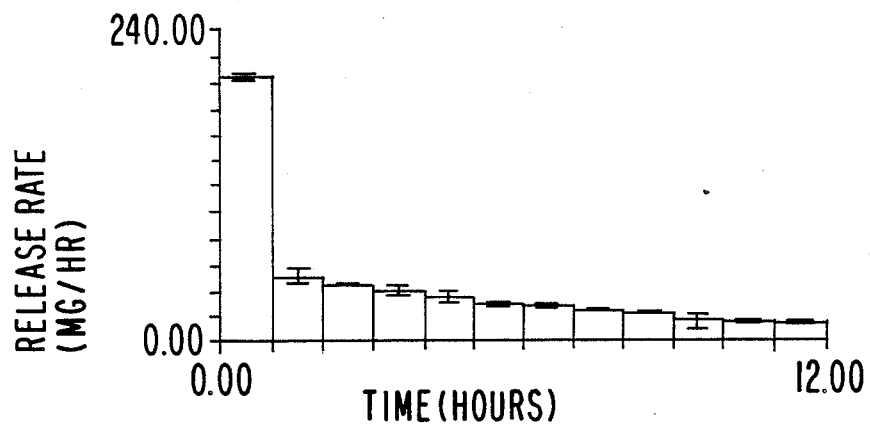
FIG. 6 is a graph illustrating immediate drug therapy followed by controlled and sustained drug therapy over a prolonged period of time for a dosage form provided by the invention.
Figure 7:
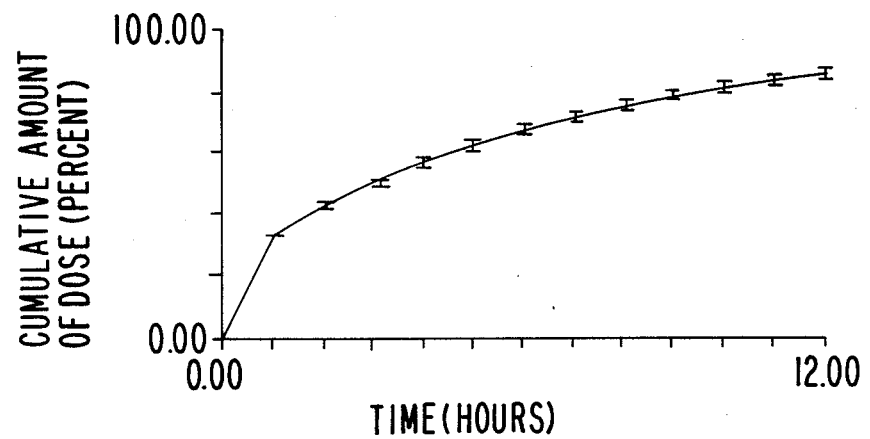
FIG. 7 is a graph depicting the cumulative dose of drug delivered from a dosage form over a period of twelve hours.

The procedure described above is followed in this example. A first lamina forming composition weighing 690 mg and comprising 58.0 wt % ibuprofen; 25.0 wt % hydroxypropylcellulose, having a number average molecular weight of 242,000; 15.0 wt % hydroxypropylmethylcellulose, having a number average molecular weight of 9,200; and, 2.0 wt % stearic acid is compressed into a first lamina. Then, a second lamina weighing 230 mg comprising 87.0 wt % ibuprofen; 10.0 wt % hydroxypropylcellulose, with 10–13 wt % hydroxypropxy content; 1.0 wt % hydroxypropylmethylcellulose, having an average number molecular weight of 9,200; and, 2.0 wt % stearic acid is deposited over a surface of the first lamina and the second lamina compressed thereto. The dosage form exhibited an initial burst of 200 mg drug within the first hour followed by a mean release rate of 30 mg/hr for the following eleven hours. The release rate pattern in mg/hr is illustrated in FIG. 6. The cumulative amount of ibuprofen released over time is illustrated in FIG. 7.

EXAMPLES 4 TO 21

The procedures described above are followed for manufacturing dosage forms comprising the following drugs: (a) 150 mg of ibuprofen in the first lamina and 50 mg of ibuprofen in the second lamina; (b) 400 mg of ibuprofen in the first lamina and 200 mg of ibuprofen in the second lamina; (c) 300 mg of aspirin in the first lamina and 200 mg of aspirin in the second lamina; (d) 400 mg of cimetidine in the first lamina and 200 mg of cimetidine in the second lamina; (e) 200 mg of umetidine in the first lamina and 100 mg of umetidine in the second lamina; (f) 500 mg of ranitidine in the first lamina and 100 mg of ranitidine in the second lamina; (9) 250 mg of acetaminophen in the first lamina and 250 mg of acetaminophen in the second lamina; (h) 250 mg of aspirin in the first lamina and 20 mg of caffeine in the second lamina; (i) 150 mg of aspirin in the first lamina and 12 mg of caffeine in the second lamina; (j) 350 mg of naproxen in the first lamina and 175 mg of naproxen in the second lamina; (k) 50 mg of phenylpropanolamine in the first lamina and 25 mg phenylpropanolamine in the second lamina; (1) 80 mg of pseudoephedrine in the first lamina and 40 mg of pseudoephedrine in the second lamina; (m) 40 mg of pseudoephedrine hydrochloride in the first lamina and 20 mg of pseudoephedrine hydrochloride in the second lamina; (n) 20 mg of pseudoephedrine in the first lamina and 1 mg of chlorpheniramine maleate in the second lamina; (o) 40 mg of pseudoephedrine in the first lamina and 3 mg of chlorpheniramine maleate in the second lamina; (p) acetaminophen in the first lamina and codeine in the second lamina; (q) ibuprofen in the first lamina and codeine in the second lamina; and (r) 100 mg phenylpropanolamine hydrochloride and 12 mg of chlorpheniramine maleate in the first lamina and 50 mg phenylpropanolamine hydrochloride and 4 mg chlorpheniramine maleate in the second lamina.

EXAMPLE 22

A dosage form for the controlled and the continuous administration of the drug 6-methoxy-alpha-methyl-2-napthaleneacetic acid is prepared by the following the above-described process of manufacture. The dosage form is manufactured by making a first lamina comprising 57 wt % of the drug, with 41 wt % low molecular weight hydroxypropylmethylcellulose having an average number molecular weight of 19,600, a number average degree of polymerization of 100 and a viscosity of 35 centipoises, and 2 wt % stearic acid; a second lamina comprising 84 wt % of the drug, 12 wt % hydroxypropylcellulose with a 10–13 wt % hydroxypropxy content and 1 wt % magnesium stearate and 3 wt % of a different hydroxypropylmethylcellulose having an average number molecular weight of 242,000, a number average degree of polymerization of 1260 and a viscosity of 100,000 centipoises measured as a 2% aqueous solution at 20° C. was laminated to the first lamina. The two lamina operated as a unit dosage form for the release of the drug at a controlled rate over time.

EXAMPLE 23

A dosage form for the controlled and the continuous administration of isosorbide dinitrate is prepared by following the above described process of manufacture. The dosage form is manufactured by making a first lamina comprising 59 wt % isosorbide/lactose, 50/50, with 42 wt % low molecular weight hydroxypropylmethylcellulose having an average number molecular weight of 27,800, a number average degree of polymerization of 145 and a viscosity of 100 centipoises; and a second lamina comprising 1 wt % hydroxypropylcellulose having a 10–13 wt % hydroxypropxy content, 97 wt % of a different hydroxypropylmethylcellulose, having an average number molecular weight of about 242,000, a number average degree of polymerization of 1260, a viscosity of 100,000 centipoises measured as a 2% aqueous solution at 20° C.; 1% ferric oxide and 1 wt % magnesium stearate.

EXAMPLE 24

Figure 8:
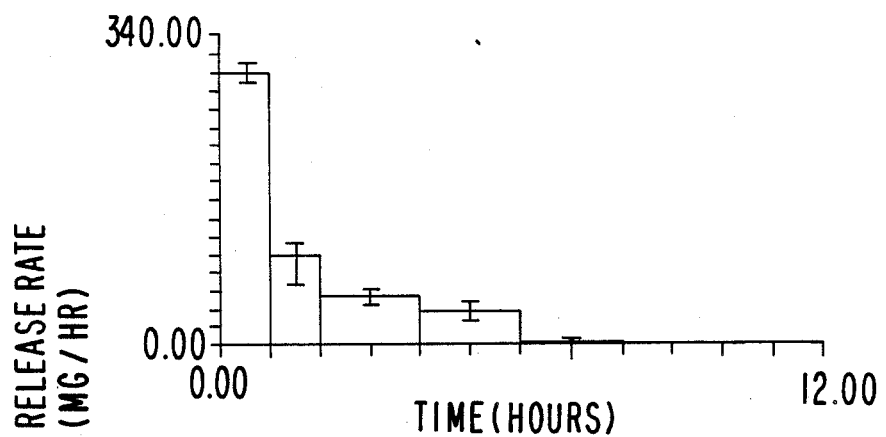
FIG. 8 is a graph that illustrates the release rate from another dosage form provided by the invention, which release rate exhibits an initial high dose of drug delivery succeeded by a sustained dose of drug.
Figure 9:
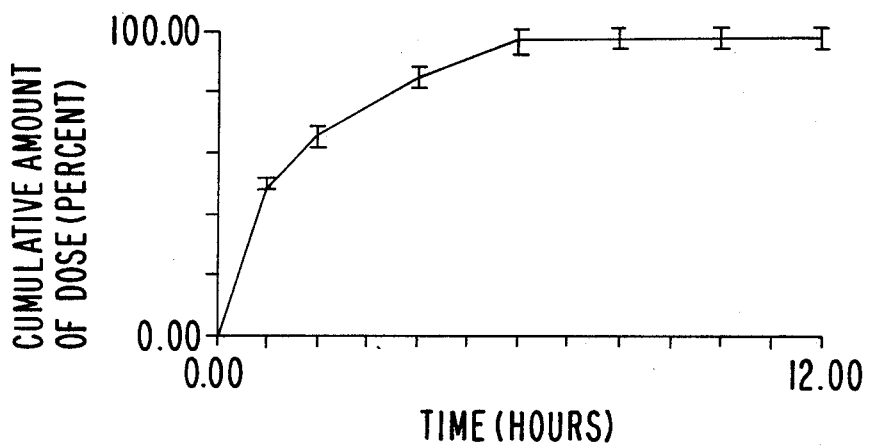
FIG. 9 is a graph that depicts the cumulative amount of drug delivered by the dosage form of FIG. 8.

A dosage form is prepared according to the procedures described in the above examples. The dosage form comprises 600 mg of ibuprofen in a lamina comprising ibuprofen 58 wt %, hydroxypropylmethylcellulose 15 wt % possessing a 242,000 molecular weight, hydroxypropylmethylcellulose 25 wt % exhibiting a 9,200 molecular weight, and stearic acid 2 wt %, the lamina weight 690 mg; and a lamina comprising 200 mg of ibuprofen in a lamina comprising ibuprofen 87 wt %, hydroxypropylcellulose 10 wt % and having a 10–13 wt % hydroxypropoxyl content, stearic acid 2 wt %, and hydroxypropylmethylcellulose 1 wt % and having a 9,200 molecular weight, with the lamina weighing 230 mg. The release rate in mg/hr for the bilaminate is seen in FIG. 8, and the cumulative amount of ibuprofen released is seen in FIG. 9. The dosage form is packaged in a fluid tight, blister package and opened when therapy is needed for its benefit.

EXAMPLE 25

Figure 10:
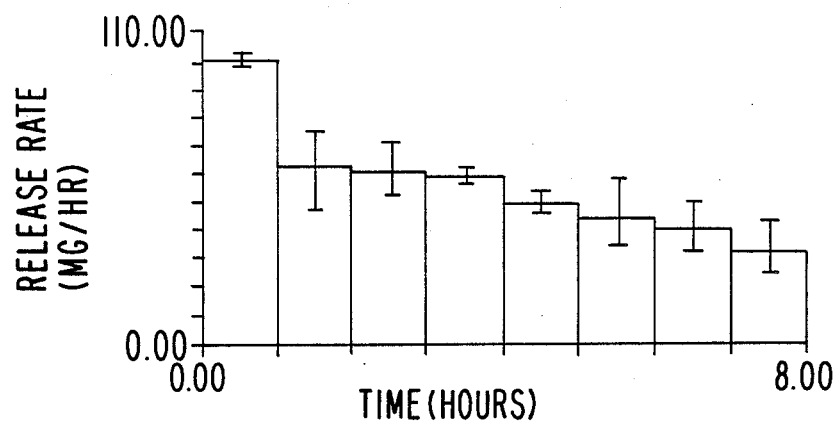
FIG. 10 is a graph depicting the release rate pattern for a controlled release dosage form comprising and releasing a different drug; and, FIG. 11 is the cumulative amount of drug released by the controlled release dosage form of FIG. 11.
Figure 11:
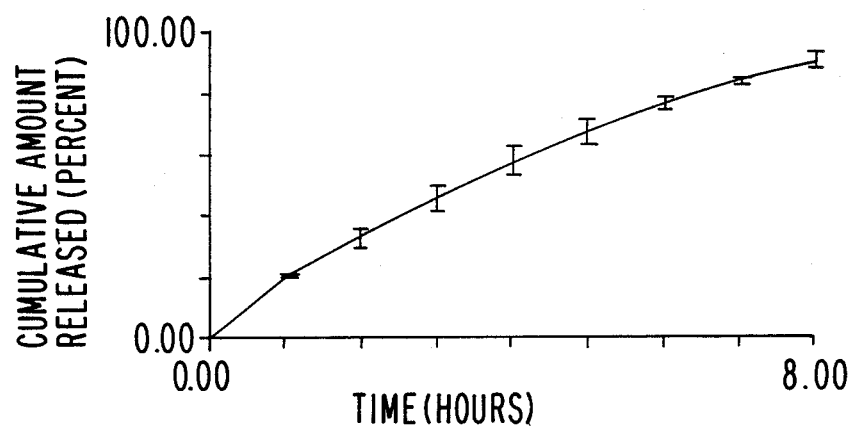

A dosage form for delivering the drug acetaminophen is prepared according to the examples set forth supra. The dosage form comprises 500 mg of acetaminophen, a first lamina weighing 662 mg and comprises 58 wt % acetaminophen; 20 wt % hydroxypropylmethylcellulose having a 242,000 molecular weight; 20 wt % hydroxypropylmethylcellulose having a 9,200 molecular weight and 2 wt % magnesium stearate; and a second lamina weighing 200 mg comprising 58 wt % acetaminophen; 15 wt % hydroxypropylmethylcellulose having a 242,000 molecular weight; 25 wt % hydroxypropylmethylcellulose having a 9,200 molecular weight, and 2 wt % magnesium stearate. The release rate in mg/hr for the dosage form is depicted in FIG. 10, and the cumulative amount released over 8 hours is seen in FIG. 11.

EXAMPLE 26

A film coating comprising 89/10/1 wt % hydroxypropylmethylcellulose/acetylated monoglyceride/titanium dioxide dispersed in water at 10% solids by weight was sprayed onto the bilaminate of Example 1. The coat was sprayed in a fluidized bed coater. The coating weighed about 2% of the total coated dosage form. The hydroxypropylmethylcellulose used in forming the coat had a degree of polymerization of about 60, a viscosity of about 2% aqueous solution of 6 centipoises and a number average molecular weight of 11,900. The coat dried in forced air at 40° C. overnight.

EXAMPLE 27

A coat comprising 56/34/4/2/2 of hydroxypropylmethylcellulose/hydroxypropylcellulose/polyethylene glycol/titanium dioxide/aluminum lake yellow No. 5 was applied by spraying in a fluidized bed coater. The hydroxypropylcellulose had a hydroxypropoxy content of not more than 80.5 wt %, a viscosity of a 2% solution in water of 6 centipoises, and a molecular weight of 73,000. The coat is coated around the bilaminate dosage forms prepared in the above examples.

EXAMPLE 28

A film coat comprising an instant release dose of drug comprising 60/40 ibuprofen/hydroxypropylmethylcellulose was applied around the dosage bilaminates of the invention. The hydroxypropylmethylcellulose had a degree of polymerization of 50, a viscosity of a 2% aqueous solution of about 3 centipoises, and a number average molecular weight of about 9,600 grams per mole.

The dosage form, in an aqueous environment of use, gives from the coat an instant dose of drug released in about 3 minutes to provide a first pulse instant release. A second pulse rapid release follows as lamina 13, prepared in the preceding examples, rapidly delivers the second pulse within 20 minutes. Lamina 12 gradually releases the balance of the dose of drug over a prolonged period of time.

EXAMPLE 29

A dosage form comprising a bilaminate was compression coated as follows: a round bilaminate tablet was made by first lightly compressing a granulation comprising 56/15/17/2 corresponding to theophylline/hydroxypropylmethylcellulose, with a degree of polymerization of 1,260 and a number average molecular weight of 242,000 grams per mole,/hydroxypropylmethylcellulose comprising a degree of polymerization of about 50 and a number average molecular weight of 9,200 grams per mole,/magnesium stearate. Onto this lamina was compressed, with 1.2 tons of pressure, a second lamina comprising 88/10/2 corresponding to theophylline/hydroxypropylcellulose, with a 13–16 hydroxypropoxyl content,/magnesium stearate. The first lamina weighed 178.6 mg and contained 100 mg of theophylline. The second lamina weighed 56.8 mg and contained 50 mg of theophylline. The tableting was done in a Manesty ® Layer Press.

Next, the resulting bilaminate was fed to a Kilian ® Press. An overcoat consisting of 50/50 lactose/microcrystalline cellulose was compressed around the bilaminate. The overcoat weighed 472 mg.

EXAMPLE 30

The procedure of example 29 is followed in this example. In this example the bilaminate was overcoated with a composition weighing 400 mg and comprising 48/48/4 of lactose/microcrystalline cellulose/theophylline to provide an additional instant release of 16 mg of theophylline.

EXAMPLE 31

Dosage form 10 of this invention provides many advantages to the dispensing art. For example, the bilaminated structure of dosage form 10 comprises a fast drug releasing lamina 13, and a slower drug releasing lamina 12. The fast drug releasing lamina 13 begins to dispense drug 14 immediately for producing an initial plasma concentration of drug 14 in a warm-blooded animal, which expression includes humans. The slower drug releasing lamina 13 releases drug 14 continuously and over time for producing a steady-state drug 14 concentration. The expression, "fast drug 14 releasing lamina 13 and slower drug 14 releasing lamina 12," as used for the purpose of this invention, denotes that lamina 13 releases drug 14 at a faster rate per unit time than does lamina 12. Also, lamina 13, because of it physical properties, provides mechanical support for lamina 12 thereby extending its drug releasing period over time. Another advantage provided by dosage form 10 is that it exhibits stomach retention during part of its drug releasing life. This stomach retention provides release of drug 14 in the stomach for drug absorption in the upper gastrointestinal tract. This retention in the upper gastrointestinal tract and delivery of drug from the stomach allows the drug to be absorbed throughout the gastrointestinal tract. This delivery system is particularly useful for drugs with known absorption windows in the upper tract.

Additional advantages of dosage form 10 are its release of drug 14 at a rate independent of the pH of the environment of use; dosage form 10 releases drug 14 at about the same rate per unit time in artificial stomach fluid and in artificial intestinal fluid; dosage form 10 releases drug 14 substantially free of irritating laboratory mucosal tissue and eventually dosage form 10 fully erodes and dissolves in the gastrointestinal tract substantially free of residual particles.

The dosage form of the invention provides an unique method for obtaining the maximum therapeutic benefit of a drug. The method comprises: (1) admitting the dosage form into a biological fluid environment of use, said dosage form comprising; (a) a drug delivery lamina comprising a cellulose ether composition means and a drug for continuously and slowly delivering the drug at a rate controlled by the lamina over an extended period up to 21 hours; and (b) a drug releasing lamina comprising a cellulosic ether composition means for delivering the drug immediately and over an unextended period up to 3 hours at a rate controlled by the lamina; and (c) delivering the drug from the unextended lamina and the extended lamina to the environment of use to provide the therapeutic effect of the drug.

The novel dosage form of this invention comprises means for the obtainment of precise release rate in the environment of use while simultaneously providing beneficial therapy to a recipient. While there has been described and pointed out features of the invention as applied to presently preferred embodiments, those skilled in the dispensing art will appreciate that various modifications, changes, additions and omissions in the dosage form illustrated and described can be made without departing from the spirit of this invention.

We claim:

1. A dosage form for delivering a drug to an environment of use, the dosage form comprising: (a) a first lamina comprising from 15 weight percent to 80 weight percent of a cellulose ether composition comprising at least one cellulose ether selected from the group consisting of a hydroxypropylmethylcellulose ether comprising a degree of polymerization of 40 to 1600, a viscosity of 2 to 225,000 and a number average molecular weight of 7,680 to 307,200; (b) a second lamina in mated relation with the first lamina, the second lamina comprising a different cellulose ether composition comprising 2 weight percent to 60 weight percent of at least one hydroxypropylcellulose comprising a hydroxypropoxyl content of 7 percent to 16 percent; (c) a dosage amount of 25 ng to 1.5 g of drug in at least one of the lamina; and, (d) a coat that surrounds the first lamina and the second lamina, said coat comprising a hydroxypropyl(alkyl)$_n$ cellulose wherein n is 0 to 1 and alkyl comprises 1 to 7 carbon atoms.

2. The dosage form for delivering a drug to an environment of use according to claim 1, wherein the first lamina and the second lamina comprise a drug.

3. The dosage form for delivering a drug to an environment of use according to claim 1, wherein the first lamina comprises more than one hydroxypropylmethylcellulose.

4. The dosage form for delivering a drug to an environment of use according to claim 1, wherein the second lamina comprises a hydroxypropylmethylcellulose.

5. A dosage form for delivering a drug to an environment of use, the dosage form comprising: (a) a first composition comprising 15 weight percent to 80 weight percent of hydroxypropylmethylcellulose; (b) a second and different composition comprising 2 weight percent to 50 weight percent of a hydroxypropylcellulose; (c) a dosage amount of 25 ng to 1.5 g of drug in at least one of the compositions; (d) a coat that surrounds the compositions, the coat comprising a hydroxypropyl(alkyl)$_n$ cellulose wherein n is 0 to 1 and the alkyl comprises 1 to 7 carbons; and (e) a dose amount of a drug in the coat.

6. The dosage form for delivering a drug to an environment of use according to claim 5, wherein the dosage form comprises a drug in both compositions.

7. The dosage form for delivering a drug to an environment of use according to claim 5, wherein the first composition comprises more than one hydroxypropylmethylcellulose.

8. The dosage form for delivering a drug to an environment of use according to claim 5, wherein the second composition comprises a hydroxypropylmethylcellulose.

9. A dosage form for delivering a drug to an environment of use, the dosage form comprising: (a) a first lamina comprising 15 weight percent to 80 percent of a hydroxypropylmethylcellulose composition; (b) a second and different lamina comprising 15 weight percent to 80 weight percent of a hydroxypropylmethylcellulose composition; (c) a dose amount of 25 ng to 1.5 g of drug in at least one of the compositions; and (d) a coat surrounding the first lamina and the second lamina, said coat comprising a hydroxypropyl(alkyl)$_n$ cellulose wherein n is 0 to 1 and the alkyl comprises from 1 to 7 carbon atoms.

10. The dosage form for delivering a drug to an environment of use according to claim 9, wherein the coat comprises a drug.

11. The dosage form for delivering a drug to an environment of use according to claim 9, wherein the first lamina comprises more than one hydroxypropylmethylcellulose.

12. The dosage form for delivering a drug to an environment of use according to claim 9, wherein the second lamina comprises more than one hydroxypropylmethylcellulose.

13. A bilaminated system for delivering a beneficial drug to an environment of use, wherein the bilaminated system comprises: a first lamina comprising up to 80 weight percent of a hydroxypropylmethylcellulose comprising a degree of polymerization of 40 to 1600, a viscosity of 2 to 225,000 and a number average molecular weight of 7,680 to 397,200; a second different lamina comprising up to 60 weight percent of a hydroxpropylcellulose comprising a hydroxypropoxyl content of 7 percent to 16 percent; and, a dosage unit amount of drug in at least one lamina, said drug comprising a member selected from the group consisting of an anticonvulsant, analgesic, anti-Parkinson, anti-inflammatory, antimicrobial, antiparasitic, antihypertensive, angiotensin converting enzyme inhibitor, antihistamine, antipyretic, adrenergic agonist, alpha-blocker, beta-adrenergic blocking, contraceptive, cardiovascular, calcium channel inhibitor, hormone, hyperglycemic, and sympathomimetic drugs.

14. A bilaminate system for delivering a beneficial drug to an environment of use, wherein the system comprises: a first lamina composition comprising up to 80 weight percent of at least one hydroxypropylmethylcellulose comprising a degree of polymerization of 40 to 1600, a viscosity of 2 to 225,000 and a number average molecular weight of 7,680 to 307,200; a second different lamina composition comprising up to 80 weight percent of at least one hydroxypropylmethylcellulose comprising a degree of polymerization of 40 to 1600, a viscosity of 2 to 225,000 and a number average molecular weight of 7,680 to 307,200; and, a dosage unit amount of drug in at least one lamina, said drug comprising a member selected from the group consisting of anticonvulsant, analgesic, anti-Parkinson, anti-inflammatory, antimicrobial, antiparasitic, antihypertensive, angiotensin enzyme inhibitor, antihistamine, antipyretic, adrenergic agonist, alpha-blocker, beta-adrenergic blocker, contraceptive, cardiovascular, calcium channel blocker, hormone, hyperglycemic, and sympathomimetic drugs.

* * * * *